US011684245B2

(12) United States Patent
Wilson

(10) Patent No.: US 11,684,245 B2
(45) Date of Patent: Jun. 27, 2023

(54) ENDOTRACHEAL TUBE WITH FULCRUM

(71) Applicant: Samuel Wilson, South Euclid, OH (US)

(72) Inventor: Samuel Wilson, South Euclid, OH (US)

(73) Assignee: Samuel Wilson, South Euclid, OH (US)

( * ) Notice: Subject to any disclaimer, the term of this patent is extended or adjusted under 35 U.S.C. 154(b) by 462 days.

(21) Appl. No.: 16/872,662

(22) Filed: May 12, 2020

(65) Prior Publication Data

US 2021/0353888 A1  Nov. 18, 2021

(51) Int. Cl.
*A61B 1/00* (2006.01)
*A61M 16/04* (2006.01)
*A61B 1/04* (2006.01)
*A61M 25/01* (2006.01)
*A61M 25/00* (2006.01)
*A61B 1/267* (2006.01)

(52) U.S. Cl.
CPC .......... *A61B 1/00154* (2013.01); *A61B 1/04* (2013.01); *A61M 16/0488* (2013.01); *A61B 1/267* (2013.01); *A61M 25/0009* (2013.01); *A61M 25/0068* (2013.01); *A61M 25/0102* (2013.01)

(58) Field of Classification Search
CPC ................................................ A61B 1/00154
See application file for complete search history.

(56) References Cited

U.S. PATENT DOCUMENTS

| 4,231,365 | A * | 11/1980 | Scarberry | A61M 16/0415 128/207.15 |
|---|---|---|---|---|
| 8,663,099 | B2 * | 3/2014 | Tydlaska | A61B 1/00101 600/185 |
| 2003/0062039 | A1 * | 4/2003 | Sniadach | A61M 16/0418 128/207.15 |

OTHER PUBLICATIONS

Kronemyer, "Prehospital First-Pass Intubation Failure Increases Physiologic Deterioration," Anesthesiology News Clinical Anesthesiology, Mar. 2, 2020, https://www.anesthesiologynews.com/Article/PrintArticle?articleID=57410 (five (5) pages).

Suppan et al., "Alternative intubation techniques vs Macintosh laryngoscopy in patients with cervical spine immobilization: systematic review and meta-analysis of randomized controlled trials," British Journal of Anaesthesia, 2016, pp. 27-36, vol. 116, No. 1 (10 pages).

Wallace et al., "A comparison of the ease of tracheal intubation using a McGrath MAC® laryngoscope and a standard Macintosh laryngoscope," Anaesthesia, 2015, pp. 1281-1285, vol. 70 (five (5) pages).

U.S. Appl. No. 29/734,410, filed May 12, 2020.

* cited by examiner

*Primary Examiner* — Christian A Sevilla
(74) *Attorney, Agent, or Firm* — Crowell & Moring LLP

(57) ABSTRACT

An endotracheal tube assembly with a plurality of curved portions is provided. A first curved portion in the endotracheal tube assembly is located adjacent to an insertion end thereof with a curvature that matches the curvature of a video laryngoscope (e.g., Glidescope®). A second curved portion in the endotracheal tube assembly is located in a central portion of the endotracheal tube assembly. The curvature of the first curved portion is greater than the curvature of the second curved portion. The first curved portion is bent at an angle of between about 120° and about 150° with respect to a straight portion of the endotracheal tube assembly. The second curved portion is bent at an angle of between about 30° and about 60° with respect to the straight portion of the endotracheal tube assembly.

17 Claims, 4 Drawing Sheets

ENDOTRACHEAL TUBE WITH FULCRUM

BACKGROUND AND SUMMARY OF THE INVENTION

The present invention is directed to a device for intubation of a patient. More specifically, the present invention is directed to an endotracheal tube assembly having a plurality of curved portions to facilitate improved intubation results in patients.

Medicine has progressed using big screens in every specialty. Although the adaptation of the videoscope to the endotracheal tube aids the medical care provider, we still have the problem of human anatomy which has natural curves in normal anatomy patients, and abnormal curves in the pathological anatomy patient. Historically, endotracheal instruments have been relatively straight. Our challenge remains to be able to ventilate, even if we cannot intubate. Where failure to intubate exists, if ventilation is possible, the patient has other options that may be initiated. Where there is an inability to ventilate, the situation becomes an emergency.

The endotracheal tube (ETT) according to the present invention (hereinafter referred to as the "Fulcrum ET") provides advantages over conventional ETTs. The Fulcrum ET has greater flexibility in the hands of a skilled practitioner's cannot-ventilate-cannot-intubate (CVCI) scenario than conventional ETTs. Previous modifications to the conventional endotracheal instrument focused on the blade, the handle, the lights, and the length. The skill set of the provider in using a conventional ETT has also been considered as a possible avenue for improvement.

Several products on the market have helped us manage the approach to intubation, manipulate the airway, and lessen the incidence of CVCI scenarios. For example, video allows us to see around curves that cannot be seen with a direct view, but this has not changed the difficulty of achieving success in some cases using currently available commercial tools.

The Fulcrum ET overcomes limitations in previous intubation devices and techniques and improves safety. A failure to intubate becomes a tragedy. Current literature does not provide a solution that achieves what the Fulcrum ET can achieve. The Fulcrum ET achieves desirable, even life-saving, results far more easily than conventional ETTs.

Tools in the arsenal for a difficult airway patient have undergone almost no significant improvement in 20 years. Although anesthesiologists have spent years developing algorithms, better fiber optics and better airway analysis to improve the line of sight, anatomical challenges remain.

Given currently available tools, practitioners have often relied on the awake intubation procedure, blind intubation (e.g., using a finger to guide advancing of the ETT into the proper position), and fiber optic intubation techniques.

Because it is both effective and cost effective, the Fulcrum ET will replace the standard nonmalleable style endotracheal tube in difficult cases, as well as in normal cases.

The following features set the Fulcrum ET apart from other ETT devices:

1. The Fulcrum ET modifies the ETT itself, not the blade or the handle.
2. The Fulcrum ET works very well with video.
3. The Fulcrum ET provides greater movement once in the airway.
4. The Fulcrum ET allows for better manipulation of the distal tip of the ETT.
5. The Fulcrum ET is comfortable and ergonomic to the hand of the provider.

Other objects, advantages and novel features of the present invention will become apparent from the following detailed description of one or more preferred embodiments when considered in conjunction with the accompanying drawings.

DETAILED DESCRIPTION OF THE DRAWINGS

Figure 1:
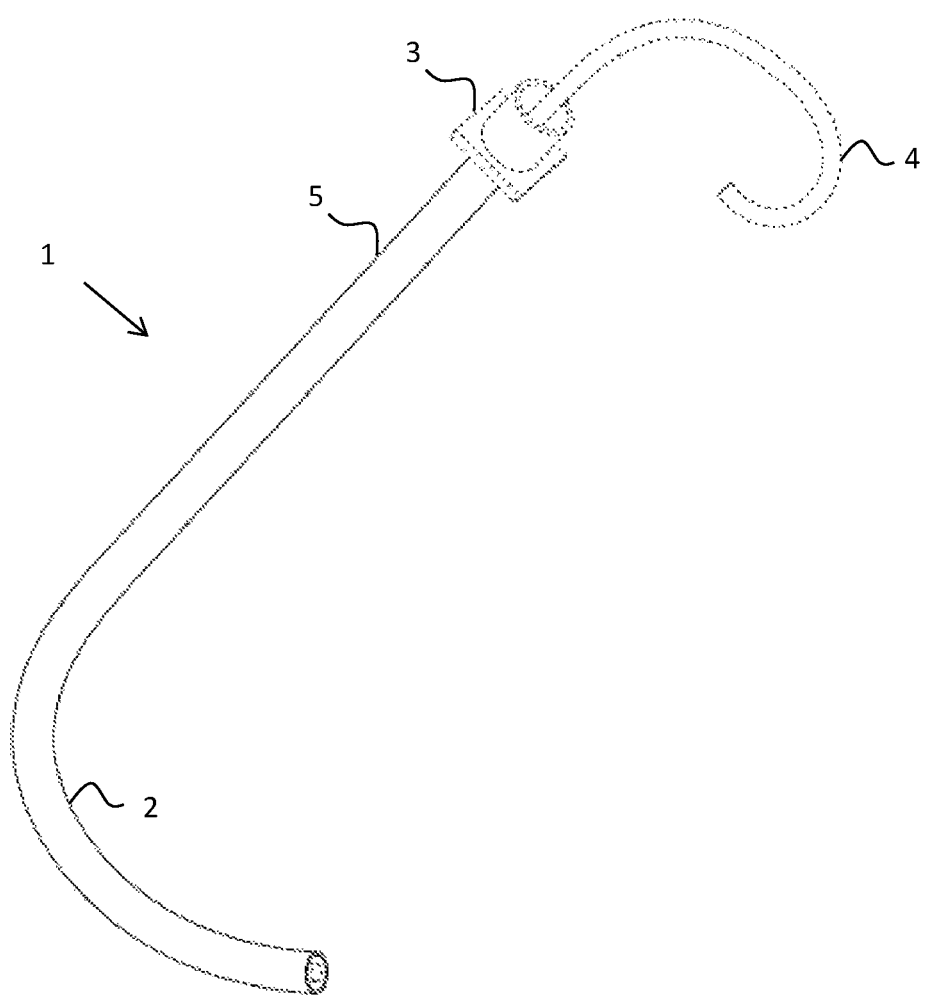
FIG. 1 illustrates a conventional endotracheal tube assembly.

FIG. 1 illustrates a conventional endotracheal tube assembly. As illustrated in FIG. 1, the conventional endotracheal tube assembly 1 includes a hollow flexible tube 5 and a stylet 4. The conventional endotracheal tube assembly 1 has only one bent portion 2, which is located near the end of the endotracheal tube assembly that is inserted into a patient's mouth (hereinafter referred to as the "insertion end"). The conventional endotracheal tube assembly 1 also includes an adaptor 3 to attach the endotracheal tube assembly to other equipment. As described above, conventional endotracheal tube assemblies suffer from a number of disadvantages that are overcome by the endotracheal tube assembly according to the present invention (the Fulcrum ET).

Figure 2:
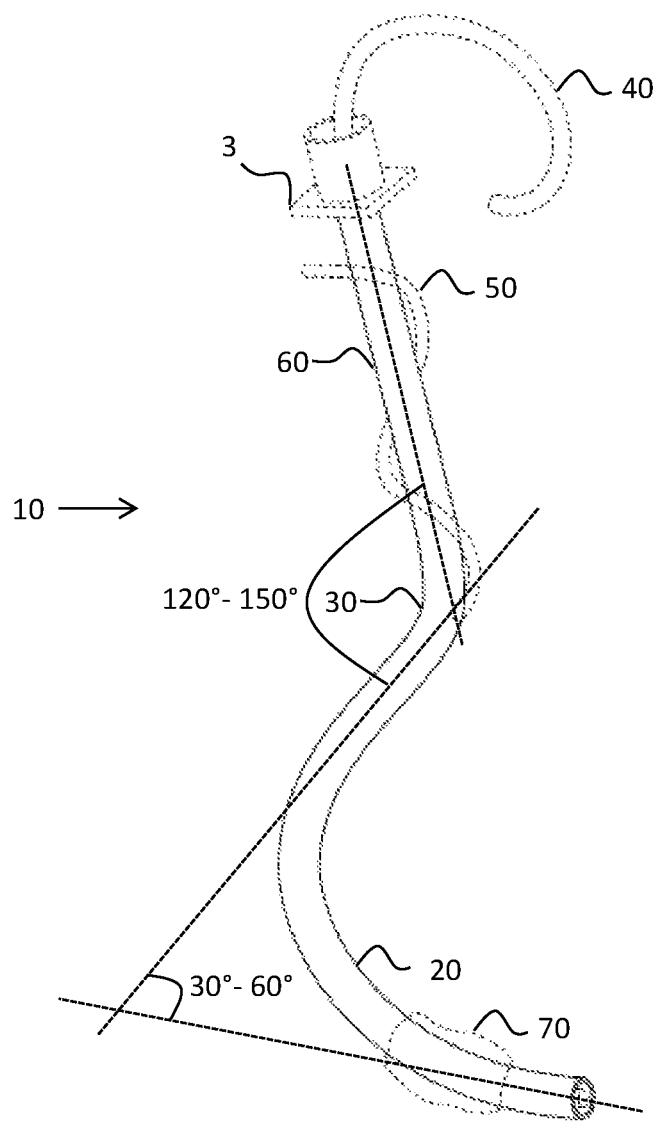
FIG. 2 illustrates a first exemplary embodiment of an endotracheal tube assembly according to the present invention.

FIG. 2 illustrates a first exemplary embodiment of an endotracheal tube assembly according to the Fulcrum ET. As illustrated in FIG. 2, the endotracheal tube assembly 10 includes at least two bent portions or curved portions. The first bent portion 20 is located near the insertion end of the endotracheal tube assembly, and the second bent portion 30 is located in a central portion of the endotracheal tube assembly. The second bent portion 30 is also referred to herein as the fulcrum of the Fulcrum ET.

As illustrated in FIG. 2, the Fulcrum ET assembly 10 includes a hollow flexible tube 60, a flexible stylet 40 disposed inside of the hollow tube 60, a balloon cuff 70 that inflates with air during an intubation to maintain a larger opening in the patient, and an external air tube 50 that is used to provide the air for inflation of the balloon cuff 70. The endotracheal tube assembly 10 has a first curved portion 20 adjacent to an insertion end of the endotracheal tube assembly and a second curved portion 30 in a central portion of the endotracheal tube assembly. A curvature of the first curved portion 20 is greater (i.e., has a tighter curve) than a curvature of the second curved portion 30. As described herein, curvature refers to an amount by which the assembly is bent or curved, where a flat assembly has no bend or curvature, and the less flat the assembly is, the more curvature it has. As illustrated in FIG. 2, the second curved portion (fulcrum) 30 is placed in the middle of the Fulcrum ET assembly 10, or just distal of the middle of the ET tube at approximately 16 to 18 cm from the insertion end of the Fulcrum ET assembly 10.

In an exemplary embodiment of the present invention, a center of the first curved portion 20 is located between 8 cm and 10 cm from the insertion end of the Fulcrum ET assembly 10. The curvature of the first curved portion 20 matches the curvature of a rigid laryngoscope (e.g., GlideScope® video laryngoscope for example), so that they can be used together. As illustrated in FIG. 2, an angle between portions of the endotracheal tube assembly on either side of a center of the second curved portion 30 is between about 120° and about 150°. An angle between portions of the endotracheal tube assembly on either side of a center of the first curved portion is between about 30° and about 60°.

A center of the second curved portion 30 is located between about 14 cm and about 20 cm from the insertion end of the Fulcrum ET assembly 10. More preferably, the center of the second curved portion 30 is located between about 16 cm and about 18 cm from the insertion end of the Fulcrum ET assembly 10. As illustrated in FIG. 2, the second curved portion 30 is bent at an angle of between about 30° and about 60° from a straight portion of the endotracheal tube assembly 10 located between the first curved portion 20 and the second curved portion 30, although larger or smaller angles for the fulcrum are also possible based on the patient anatomy. For example, smaller patients (e.g., children) would use a Fulcrum ET assembly with a fulcrum 30 having a bend of about 60° or so while larger patients would use a Fulcrum ET assembly with a fulcrum 30 having a bend of about 30° or possibly a few degrees less. In accordance with the curvature of the second curved portion 30, the angle between portions of the endotracheal tube assembly on either side of the center of the second curved portion is between about 120° and about 150°.

The Fulcrum ET assembly addresses the difficulty that medical providers have with patient anatomy and line of sight when intubating a patient. The "J" Shape of the malleable fulcrum ET distal segment near the insertion end is shaped in the contour of the oral pharyngeal anatomy. See FIG. 2. Once the fulcrum (second curved portion) 30 reaches the vocal cords, a slight clockwise rotation allows the Fulcrum ET tube tip to be further, easily, placed into the upper tracheal tree than conventional devices, thus facilitating improved intubation.

Figure 3:
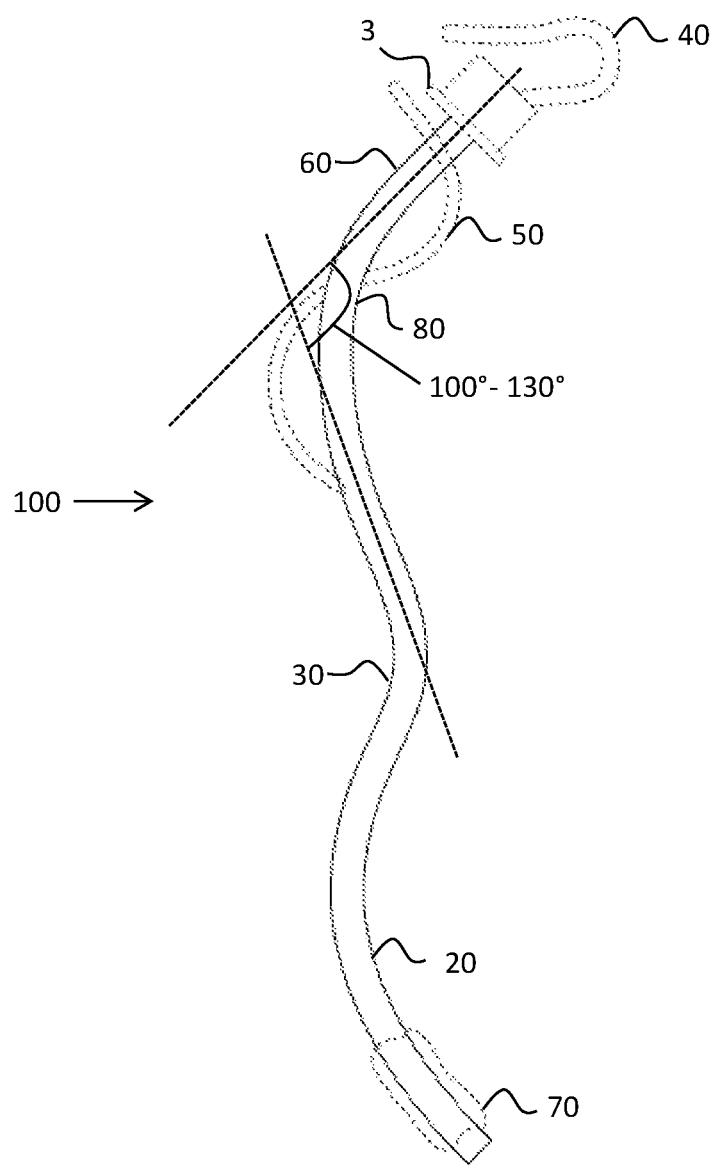
FIG. 3 illustrates a second exemplary embodiment of an endotracheal tube assembly according to the present invention.

As illustrated in FIG. 3, a second exemplary embodiment of the Fulcrum ET assembly includes a third curved portion 80 formed in the Fulcrum ET assembly between the second curved portion and an end of the Fulcrum ET assembly at which the adaptor is disposed. The angle between the portions of the endotracheal tube assembly on either side of a center of the third curved portion is between about 100° and about 130°. A center of the third curved portion 80 is located between about 25 cm and about 28 cm from the insertion end of the Fulcrum ET assembly 10. The third curved portion 80 further improves the ability to insert the Fulcrum ET assembly during intubation. The third curved portion 80 also stabilizes clockwise rotation in the anterior airway.

All prior modifications to conventional ETTs have focused on achieving success with the direct vision approach. With this approach, the medical practitioner looks down the oropharynx into the posterior pharynx attempting to visualize the tissues surrounding the vocal cords and ultimately the vocal cords themselves. The inability to intubate often involves not being able to physically reach the cords with current tools. Even where a practitioner may be able to see, the anatomy may prevent reach up to the cords.

In the past, health care professionals have used two types of laryngoscope: the Macintosh and the Miller. The Macintosh is curved and the Miller is straight. The goal in using either is to allow the provider a direct view of the patient's anatomy. When that view cannot be obtained, we are often not successful in intubating a patient. A few have modified the distal end of the ET tube hoping to reach the area not seen, mentally with an image of where it should be. This is known as blind intubation.

A laryngoscope enabled for use with a video camera (e.g., GlideScope® or McGRATH™) offers a video view of the anatomy during an intubation. Yet, there remain cases where the CVCI scenario exists due to anatomical challenges not accommodated by these devices. The GlideScope® stylet is rigid and longer in length than a normal intubating ETT stylet. Rigidity without the curve prevents clockwise or counter clockwise movement and anterior reach, butting anterior upon the posterior surfaces of the oral pharynx, and butting the esophageal wall, or teeth on the posterior surface. For example, the normal rigid GlideScope® stylet may not allow the last about 3 to about 4 cm of the GlideScope® stylet to be inserted with any manipulation.

The following describes limitations of conventional ET tools in critical situations as compared to the Fulcrum ET. Where there is the presence of a cervical spine injury in a patient, there is a strong desire to limit any manipulation of the injured patient's cervical spine, and use of a videoscope-enabled device (e.g., GlideScope® or McGRATH™ tool) is recommended. This is described, for example, in the article "Alternative intubation techniques vs Macintosh laryngoscopy in patients with cervical spine immobilization: systematic review and meta-analysis of randomized controlled trials" in the British Journal of Anesthesia published Jun. 30, 2015. Also, the Macintosh blade is being used more and more by trainee providers.

In the article "A comparison of the ease of tracheal intubation using a McGrath MAC® laryngoscope and a standard Macintosh laryngoscope" by Wallace et al, published Sep. 4, 2015 in Anesthesia, the authors found higher median Intubation Difficulty Scores with the McGrath MAC® as a direct laryngoscope (DL) than when using it as an indirect video laryngoscope, or when using the Macintosh laryngoscope. This was mirrored in the subjective user reporting of difficulty for each method. The authors concluded that they cannot recommend that the McGRATH™ video laryngoscope be used as a direct laryngoscope device in place of the Macintosh. The Fulcrum ET reduces this limitation. The Fulcrum ET works well for these known failures.

Estimates report that 50 million intubations are performed worldwide and are growing at an annual rate of 5%. See Http://www.inc.co.ik/pages/intumed.htm. Thus, improved intubation results are becoming more important. As described above, the Fulcrum ET provides for improved intubation results.

With regard to the needs of different patients, the Fulcrum ET is adaptable to a variety of patients. For example, in patients with overbites, the airway is more anterior and more proximal in the neck. As such, patients with an overbite will require about 110° to about 150° bend at the first bent position 20, for example about a 130° bend at the first bent position 20. Within this range, children will have a tighter bend at the first bent position 20, closer to about 110° bend at the first bent position 20 since the anatomy of a child is more acute. Patients with upper lip overbite will benefit from using the Fulcrum ET tube.

Larger-bodied patients, often obese, may have more tissue in the airway. The Fulcrum ET allows the DL provider to follow the shape of the GlideScope® or the McGRATH™, to the point of cord entry. The clear visual and the ease in following the curve using the Fulcrum ET provides significant advantages over conventional devices. In a small mouth patient, for example, where there is almost no flexibility in opening, the use of the Fulcrum ET is advantageous because it mimics the curve of conventional laryngoscopes (e.g., the GlideScope® and the McGRATH™). Thus, following the path to the picture provided by these devices facilitates intubation.

The location of the fulcrum gives providers a fixed point of flexion at the mouth, allowing the tip of an endotracheal tube more anterior range of movement; thus, the Fulcrum ET provides improved anterior reach and provides numerous unexpected benefits in improved intubation outcomes.

Unrecognized pathology for manual DL is less of a concern when the provider can see the area of intended placement, even if there is disease along the way. Again, the Fulcrum ET is valuable for greater anterior reach and comfort in stressful circumstances. The provider can see more using the video. And the provider can reach farther using the Fulcrum ET tube. In particular, reach improvement can be about 4 cm or more. Also, clockwise rotation can facilitate tip direction. Each current intubating device has more than one size, with a significant difference being in the tip width. In the small mouth patient, just the size alone limits the maneuverability during intubation. The Fulcrum ET tube, including when aided by the camera view, provides an improvement over conventional devices.

The following descriptions exemplify advantages of the Fulcrum ET assembly over conventional devices as explained through particular situations in which patients have benefited from the Fulcrum ET assembly. These outcomes provided unexpected and beneficial results in patient intubation. In some cases, results obtained by using the Fulcrum ET are nothing short of life-saving.

Advantageous Case 1:

The surgical patient had a history of difficulty with intubation. More than one experienced provider had failed to intubate this patient despite following the American Society of Anesthesiologists (ASA) algorithm for intubation. At that time, the surgical case was canceled because of an inability to intubate. On a return visit to the operating room, when the same patient presented, while performing DL from the GlideScope®, although the anesthesiologist could clearly visualize the vocal cords of the patient, the traditional rigid stylet was not successful. However, the abnormal anatomy was overcome using the Fulcrum ET. The Fulcrum ET was placed without event—without time delay, without increasing risk, without concern, and without unnecessary trauma to the patient, all due to the confidence of the Fulcrum ET in allowing additional reach. The Fulcrum ET provides the opportunity to minimize trauma with intubation. It is a gentle manipulation, visibility is easier, less strength is required due to greater visibility, and greater reach that follows the path of visibility is achieved.

Advantage Case 2:

A robotic patient under general anesthesia had become extubated. In this critical moment, the patient was in a deep Trendelenburg position. The use of the GlideScope® with the Fulcrum ET tube allowed safe replacement of that patient's airway, while the patient was in a compromised physical position.

Advantage Case 3:

The overhead paging system (STAT) called for assistance to intubate an obese patient (BMI greater than 35) who was scheduled for a robotic procedure. Three providers had attempted and failed intubation using traditional ET tubes. The airway was traumatized by prior attempts. The GlideScope® was used, providing a clear view of the airway trauma, swelling, and bleeding. With the Fulcrum ET and a slight clockwise rotation advancing as rotating, the tip floated forward into the proximal trachea region. The anesthesiologist reached the cords and secured the airway by this method.

Advantage Case 4:

In using the video device to assist, usual DL body position or stance posture is different from when you have a hand held DL using a Miller or a Macintosh blade. The provider is more flexed and more bent forward with one's neck and the head tilted slightly off to the side as the provider attempts to look down the airway of the patient. With the Fulcrum ET used with a video GlideScope® or any other video device, the provider is standing straight, and has a better ergonomic approach to successfully complete the intubation. Using the video in combination with the Fulcrum ET, there is often less force applied to the intubating device upon the soft tissue of the oral airway.

With the increased success facilitated by using the Fulcrum ET in difficult intubations, providers undergo less risk of infectious disease exposure and contamination. By way of example, risk of exposure to Covid-19 may be reduced by use of the Fulcrum ET because providers may maintain a greater distance from a patient's airway and may complete intubation in fewer attempts and with involvement of fewer providers.

Figure 4:
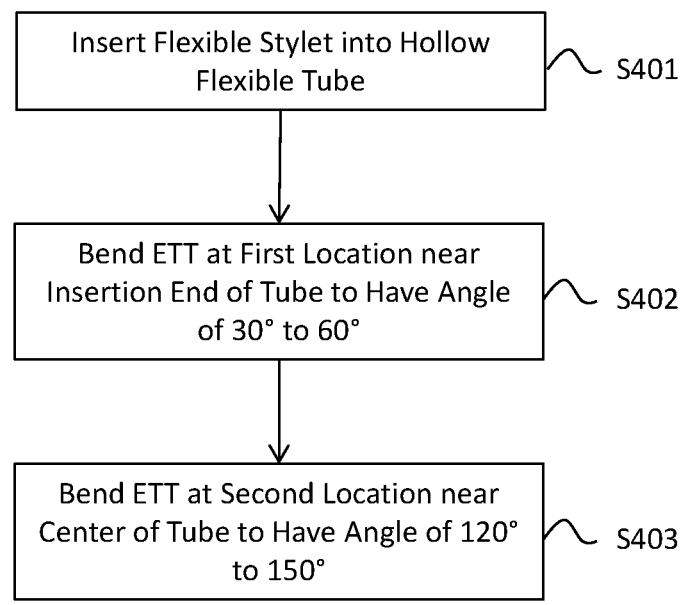
FIG. 4 illustrates an exemplary embodiment of a method for manufacturing an endotracheal tube assembly according to the present invention.

FIG. 4 illustrates an exemplary embodiment of a method for manufacturing a Fulcrum ET assembly according to the present invention. As illustrated in FIG. 4, the method begins with step S401 in which a flexible stylet 40 is inserted into a hollow flexible tube 60 to form an endotracheal tube assembly. The hollow flexible tube 60 includes the adaptor 3, the air tube 50 and the balloon cuff 70. In step S402, the endotracheal tube assembly is bent in a first location near an insertion end of the endotracheal tube assembly to create a first curved portion. The first curved portion is preferably bent in such a manner that a center of the first curved portion is located between 8 cm and 10 cm from the insertion end of the endotracheal tube assembly. The curvature of the first curved portion matches the curvature of a rigid video laryngoscope (e.g., GlideScope®) so that they can be used together. As illustrated in FIG. 2, an angle between a straight portion of the Fulcrum ET assembly, located between the first curved portion and the second curved portion, and the first curved portion is between about 120° and about 150°.

In step S403, the endotracheal tube assembly is bent in a second location in a central portion thereof to form a second curved portion (fulcrum) in the middle of the Fulcrum ET assembly. A center of the second curved portion is located between about 14 cm and about 20 cm from the insertion end of the Fulcrum ET assembly. More preferably, the center of the second curved portion is located between about 16 cm and about 18 cm from the insertion end of the Fulcrum ET assembly 10. As illustrated in FIG. 2, the second curved portion is bent at an angle of between about 30° and about 60° from a straight portion of the Fulcrum ET assembly located between the first curved portion and the second curved portion, although larger or smaller angles for the fulcrum are also possible based on the patient anatomy. In accordance with the curvature of the second curved portion, an angle between portions of the Fulcrum ET assembly on either side of a center of the second curved portion is between about 120° and about 150°.

In a second exemplary embodiment of the method, a third curved portion is formed in the Fulcrum ET assembly by bending the assembly in a third location between the second curved portion and an end of the Fulcrum ET assembly at which the adaptor is disposed. The angle between the portions of the Fulcrum ET assembly on either side of a center of the third curved portion is between about 100° and about 130°.

The foregoing disclosure has been set forth merely to illustrate the invention and is not intended to be limiting. Since modifications of the disclosed embodiments incorporating the spirit and substance of the invention may occur to persons skilled in the art, the invention should be construed to include everything within the scope of the appended claims and equivalents thereof.

What is claimed is:

1. An endotracheal tube assembly, comprising:
   a hollow tube that is flexible; and
   a flexible stylet disposed inside of the hollow tube;
   wherein the endotracheal tube assembly has a first curved portion adjacent to an insertion end of the endotracheal tube assembly and a second curved portion in a central portion of the endotracheal tube assembly;
   wherein a curvature of the first curved portion is greater than a curvature of the second curved portion;
   wherein an angle between portions of the endotracheal tube assembly on either side of a center of the second curved portion is between about 120° and about 150°; and
   wherein an angle between portions of the endotracheal tube assembly on either side of a center of the first curved portion is between about 30° and about 60°.

2. The endotracheal tube assembly according to claim 1, wherein a center of the first curved portion is located between about 8 cm and about 10 cm from the insertion end of the endotracheal tube assembly.

3. The endotracheal tube assembly according to claim 1, wherein a center of the second curved portion is located between about 14 cm and about 16 cm from the insertion end of the endotracheal tube assembly.

4. The endotracheal tube assembly according to claim 1, wherein the curvature of the first curved portion matches a curvature of a video laryngoscope.

5. The endotracheal tube assembly according to claim 1, wherein the second curved portion is bent at an angle of between about 30° and about 60° from a straight portion of the endotracheal tube assembly located between the first curved portion and the second curved portion.

6. The endotracheal tube assembly according to claim 2, wherein a center of the second curved portion is located between about 14 cm and about 16 cm from the insertion end of the endotracheal tube assembly.

7. The endotracheal tube assembly according to claim 3, wherein the second curved portion is bent at an angle of between about 30° and about 60° from a straight portion of the endotracheal tube assembly located between the first curved portion and the second curved portion.

8. The endotracheal tube assembly according to claim 1, wherein an angle between a straight portion of the endotracheal tube assembly, located between the first curved portion and the second curved portion, and the first curved portion is between about 120° and about 150°.

9. A method for manufacturing an endotracheal tube assembly, comprising:
   inserting a flexible stylet into a hollow flexible tube to form the endotracheal tube assembly;
   bending the endotracheal tube assembly at a first location adjacent to an insertion end of the endotracheal tube assembly to form a first curved portion; and
   bending the endotracheal assembly at a second location in a central portion of the endotracheal tube assembly to form a second curved portion;
   wherein a curvature of the first curved portion is greater than a curvature of the second curved portion;
   wherein an angle between portions of the endotracheal tube assembly on either side of a center of the first curved portion is between about 30° and about 60°; and
   wherein an angle between portions of the endotracheal tube assembly on either side of a center of the second curved portion is between about 120° and about 150°.

10. The method according to claim 9, wherein a center of the first curved portion is located between about 8 cm and about 10 cm from the insertion end of the endotracheal tube assembly.

11. The method according to claim 9, wherein a center of the second curved portion is located between about 14 cm and about 16 cm from the insertion end of the endotracheal tube assembly.

12. The method according to claim 9, wherein the curvature of the first curved portion matches a curvature of a video laryngoscope.

13. The method according to claim 9, wherein the second curved portion is bent at an angle of between about 30° and about 60° from a straight portion of the endotracheal tube assembly located between the first curved portion and the second curved portion.

14. The method according to claim 11, wherein the second curved portion is bent at an angle of between about 30° and about 60° from a straight portion of the endotracheal tube assembly located at an opposite end from the insertion end.

15. The method according to claim 9, wherein an angle between a straight portion of the endotracheal tube assembly, located between the first curved portion and the second curved portion, and the first curved portion is between about 120° and about 150°.

16. An endotracheal tube assembly, comprising:
   a hollow tube that is flexible; and
   a flexible stylet disposed inside of the hollow tube;
   wherein the endotracheal tube assembly has a first curved portion adjacent to an insertion end of the endotracheal tube assembly and a second curved portion in a central portion of the endotracheal tube assembly;
   wherein a curvature of the first curved portion is greater than a curvature of the second curved portion;
   wherein a center of the first curved portion is located between about 8 cm and about 10 cm from the insertion end of the endotracheal tube assembly; and
   wherein a center of the second curved portion is located between about 14 cm and about 16 cm from the insertion end of the endotracheal tube assembly.

17. The endotracheal tube assembly of claim 16 wherein an angle between portions of the endotracheal tube assembly on either side of a center of the second curved portion is between about 120° and about 150°, and wherein an angle between portions of the endotracheal tube assembly on either side of a center of the first curved portion is between about 30° and about 60°.

* * * * *